United States Patent
McCollough et al.

(10) Patent No.: US 11,143,767 B2
(45) Date of Patent: Oct. 12, 2021

(54) METHODS FOR OPTIMIZING IMAGING TECHNIQUE PARAMETERS FOR PHOTON-COUNTING COMPUTED TOMOGRAPHY

(71) Applicant: Mayo Foundation for Medical Education and Research, Rochester, MN (US)

(72) Inventors: Cynthia H. McCollough, Byron, MN (US); Zhoubo Li, Libertyville, IL (US); Shuai Leng, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/912,656

(22) Filed: Jun. 25, 2020

(65) Prior Publication Data
US 2020/0326439 A1  Oct. 15, 2020

Related U.S. Application Data

(62) Division of application No. 15/552,637, filed as application No. PCT/US2016/019097 on Feb. 23, 2016, now Pat. No. 10,732,309.
(Continued)

(51) Int. Cl.
*G01T 7/00* (2006.01)
*A61B 6/03* (2006.01)
(Continued)

(52) U.S. Cl.
CPC .............. *G01T 7/005* (2013.01); *A61B 6/032* (2013.01); *A61B 6/4241* (2013.01); *A61B 6/482* (2013.01);
(Continued)

(58) Field of Classification Search
CPC ....... G01T 7/005; G01T 1/2985; G01D 18/00; A61B 6/032; A61B 6/4241; A61B 6/482; A61B 6/5258; A61B 6/545
See application file for complete search history.

(56) References Cited

U.S. PATENT DOCUMENTS

| | | |
|---|---|---|
| 6,701,025 B1 | 3/2004 | Avinash |
| 8,929,508 B1 * | 1/2015 | Alvarez ............... G01N 23/087 378/18 |

(Continued)

FOREIGN PATENT DOCUMENTS

WO  2014176328 A1  10/2014

OTHER PUBLICATIONS

PCT International Search Report and Written Opinion, PCT/US2016/019097, dated Jul. 27, 2016, 20 pages.

*Primary Examiner* — Marcus H Taningco
(74) *Attorney, Agent, or Firm* — Quarles & Brady LLP

(57) ABSTRACT

Described here are systems and methods for optimization techniques for automatically selecting x-ray beam spectra, energy threshold, energy bin settings, and other imaging technique parameters for photon-counting detector computed tomography ("PCCT"). The techniques described here are generally based on subject or object size, material of interest, and location of the target material. Advantageously, the optimizations can be integrated with different PCCT systems to automatically select optimal imaging technique parameters before scanning a particular subject or object.

9 Claims, 6 Drawing Sheets

Related U.S. Application Data

(60) Provisional application No. 62/119,628, filed on Feb. 23, 2015.

(51) Int. Cl.
    *A61B 6/00* (2006.01)
    *G01D 18/00* (2006.01)
    *G01T 1/29* (2006.01)

(52) U.S. Cl.
    CPC ............ *A61B 6/5258* (2013.01); *A61B 6/545* (2013.01); *G01D 18/00* (2013.01); *G01T 1/2985* (2013.01)

(56) References Cited

U.S. PATENT DOCUMENTS

| | | |
|---|---|---|
| 9,959,640 B2 | 5/2018 | Koehler |
| 2002/0150302 A1 | 10/2002 | McCarthy |
| 2007/0083114 A1 | 4/2007 | Yang |
| 2009/0033328 A1 | 2/2009 | Feiweier |
| 2010/0060509 A1* | 3/2010 | Chambers ........... G01S 13/0209 342/22 |
| 2014/0003689 A1 | 1/2014 | Asma |
| 2014/0314211 A1 | 10/2014 | Zou |
| 2015/0042783 A1* | 2/2015 | Ober ...................... G02B 21/16 348/80 |
| 2015/0077109 A1 | 3/2015 | Grodzki |
| 2015/0192510 A1* | 7/2015 | Piestun .............. G01N 15/1456 702/151 |
| 2016/0044255 A1* | 2/2016 | Bewersdorf ........... H04N 5/378 348/241 |
| 2017/0363725 A1* | 12/2017 | Ignjatovic ........... G01S 15/8915 |

* cited by examiner

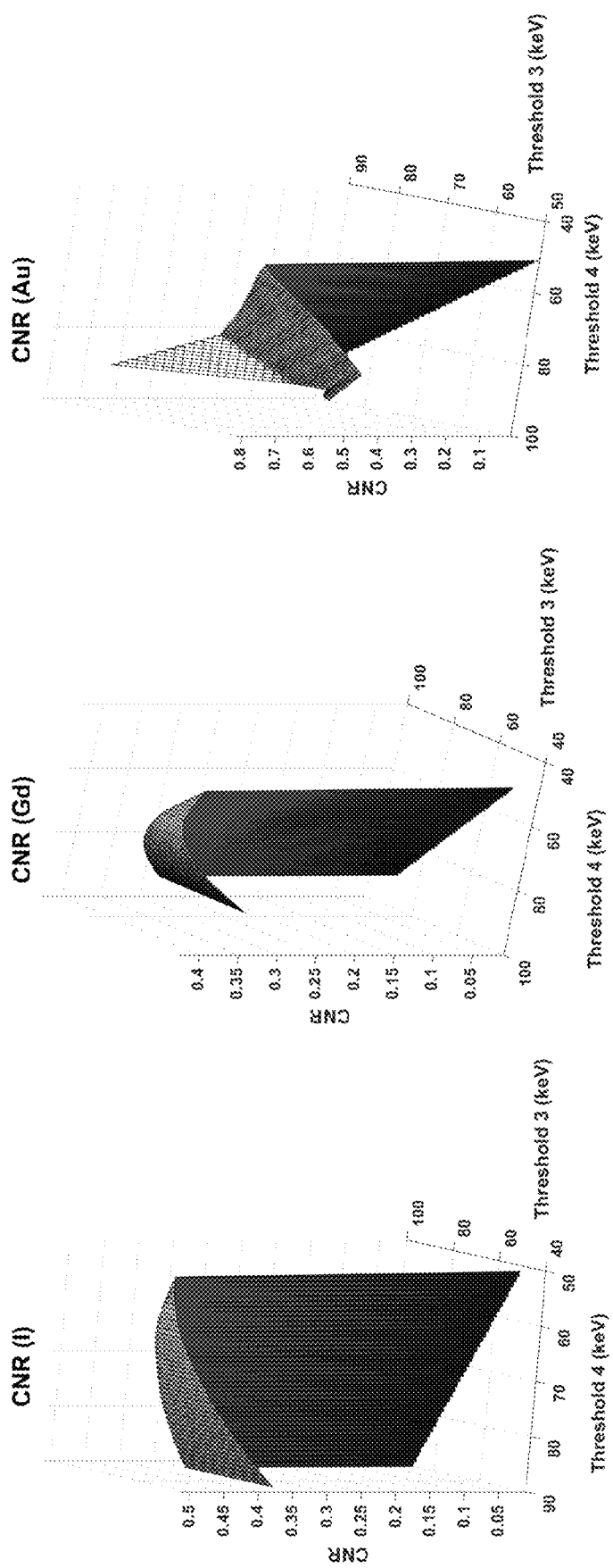

METHODS FOR OPTIMIZING IMAGING TECHNIQUE PARAMETERS FOR PHOTON-COUNTING COMPUTED TOMOGRAPHY

CROSS-REFERENCE TO RELATED APPLICATIONS

This application is a divisional of U.S. patent application Ser. No. 15/552,637 filed on Aug. 22, 2017, which represents the national stage entry of PCT International Application No. PCT/US2016/019097 filed on Feb. 23, 2016 and claims the benefit of U.S. Provisional Patent Application Ser. No. 62/119,628, filed on Feb. 23, 2015, the contents of which are hereby incorporated by reference as if set forth in their entirety herein.

STATEMENT REGARDING FEDERALLY SPONSORED RESEARCH

This invention was made with government support under EB016966 awarded by the National Institutes of Health. The government has certain rights in the invention.

BACKGROUND OF THE INVENTION

The field of the invention is systems and methods for x-ray imaging, including x-ray computed tomography ("CT"). More particularly, the invention relates to systems and methods for photon-counting detector computed tomography ("PCCT").

PCCT systems have the potential to greatly increase the medical benefits of CT. Unlike "traditional" CT detectors, which integrate the charge generated by x-ray photon interactions in the detector but provide no specific energy information regarding individual photons, photon-counting detectors record the energy deposited by each individual photon interacting with the detector. PCCT systems can thus be used to differentiate materials, such as a contrast agent in the blood and calcifications that may otherwise be indistinguishable in traditional CT systems.

PCCT systems can also be used to improve the signal-to-noise ratio ("SNR") by reducing electronic noise. In general, PCCT systems produce less image noise for the same patient dose than traditional CT systems and, hence, can be more dose efficient than these conventional CT systems. Also, PCCT systems can improve SNR by assigning optimal, energy dependent weighting factors to the detected photons and can achieve additional SNR improvements by completely or partially rejecting scattered photons. Further still, use of a PCCT system allows measurement of transmitted, energy-resolved spectra from a single exposure at one tube potential.

PCCT systems can perform multi-energy measurements for N≥2 energy levels. In some configurations, measurements are obtained on the same pixel with N identical energy thresholds on the same detector element. Images with higher energy resolution can then be generated based on a subtraction between measurements from the same pixel. In some other configurations, cross-pixel measurements are obtained with different energy thresholds on the same detector element. Images with higher energy resolution are then generated based on a subtraction between measurements from different pixels.

Selection of the x-ray tube spectra, energy thresholds, and energy bins that are used in PCCT has a significant effect on the resulting image quality, material decomposition capability, and radiation dose imparted to patients. Because the degree of freedom for optimizing the selection of the x-ray tube spectra, energy thresholds, and energy bins is very high, it would be desirable to have a systematic optimization scheme for selecting these parameters before initiating a patient scan.

SUMMARY OF THE INVENTION

The present invention overcomes the aforementioned drawbacks by providing a method for determining imaging technique parameters for a photon-counting computed tomography ("PCCT") system using a signal estimation and noise propagation analysis. The method includes selecting imaging technique parameters for the PCCT system and generating a first signal estimate and a first noise estimate associated with the imaging technique parameters. Optimal imaging technique parameters are then computed using an optimization based on a signal estimation and noise propagation analysis. Each iteration of the optimization includes the following steps. The imaging technique parameters are updated and a second signal estimate and a second noise estimate associated with the updated imaging technique parameters are generated. A first figure of merit value is then generated using the first signal estimate and the first noise estimate, and a second figure of merit value is generated using the second signal estimate and the second noise estimate. A stopping criterion based on comparing the first figure of merit value and the second figure of merit value is then evaluated. When the stopping criterion is not satisfied, the second signal estimate is stored as the first signal estimate and the second noise estimate is stored as the first noise estimate before again updating the imaging technique parameters. When the stopping criterion is satisfied, the updated imaging technique parameters are stored as optimal imaging technique parameters for later use with the PCCT system.

It is another aspect of the invention to provide a method for determining imaging technique parameters for a PCCT system using an overall Cramer-Rao Lower Bound ("CRLB") value. The method includes selecting imaging technique parameters for the PCCT system and computing optimal imaging technique parameters using an optimization. Each iteration of the optimization includes the following steps. A CRLB value is computed for each of a plurality of different combinations of detector channels and projection angles associated with the PCCT system and based on the imaging technique parameters. An overall CRLB value is then computed as a weighted summation of the CRLB values. A stopping criterion based on the overall CRLB value is then evaluated. When the stopping criterion is not satisfied, the imaging technique parameters are updated and additional CRLB values are computed based on the updated imaging technique parameters. When the stopping criterion is satisfied, the imaging technique parameters are stored as optimal imaging technique parameters for later use with a PCCT system.

It is yet another aspect of the invention to provide a method for determining imaging technique parameters for a PCCT system using a model observer. The method includes selecting imaging technique parameters for the PCCT system and computing optimal imaging technique parameters using an optimization. Each iteration of the optimization includes the following steps. A virtual scan is performed to generate images indicative of a signal estimate and a noise estimate associated with the imaging technique parameters. A figure of merit value is computed by applying a model observer to the generated images. A stopping criterion based on the figure of merit value is then evaluated. When the stopping criterion is not satisfied, the imaging technique parameters are updated and another virtual scan is performed using the updated imaging technique parameters. When the stopping criterion is satisfied, the imaging technique parameters are stored as optimal imaging technique parameters for later use with the PCCT system.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 2A-2C illustrate examples of noise propagation analysis-based optimizations for two energy thresholds for imaging different contrast agents using PCCT;

DETAILED DESCRIPTION OF THE INVENTION

Described here are systems and methods for optimization techniques for automatically selecting imaging technique parameters for photon-counting detector computed tomography ("PCCT"). Imaging technique parameters can include x-ray beam spectra settings, energy threshold settings, and energy bin settings. The techniques described here are generally based on patient size, material of interest, and location of the targeted material. Advantageously, the optimizations can be integrated with different PCCT systems to automatically select optimal imaging technique parameters—including x-ray tube spectra, energy thresholds, and energy bins—before scanning a particular patient.

In some embodiments, the optimization of the imaging technique parameters implements a signal estimation and noise propagation analysis. In some other embodiments, the optimization of the imaging technique parameters implements an overall Cramer-Rao Lower Bound ("oCRLB") calculation. In still other embodiments, the optimization of the imaging technique parameters implements a model observer method. The choice between how to implement the optimization technique can be based on the clinical task at hand. For instance, the choice can be based in part on whether it is desired to maximize contrast-to-noise ratio ("CNR"); to estimate basis material densities, such as by using material decomposition; or to image contrast materials, such as by using K-edge subtraction imaging.

Signal Estimation and Noise Propagation Analysis

As mentioned above, in some embodiments, optimization of the imaging technique parameters for a PCCT system can be based on a noise propagation analysis that implements a general noise model for PCCT images. As will be described below, the noise model can be selected based on the acquisition scheme to be implemented.

Figure 1:
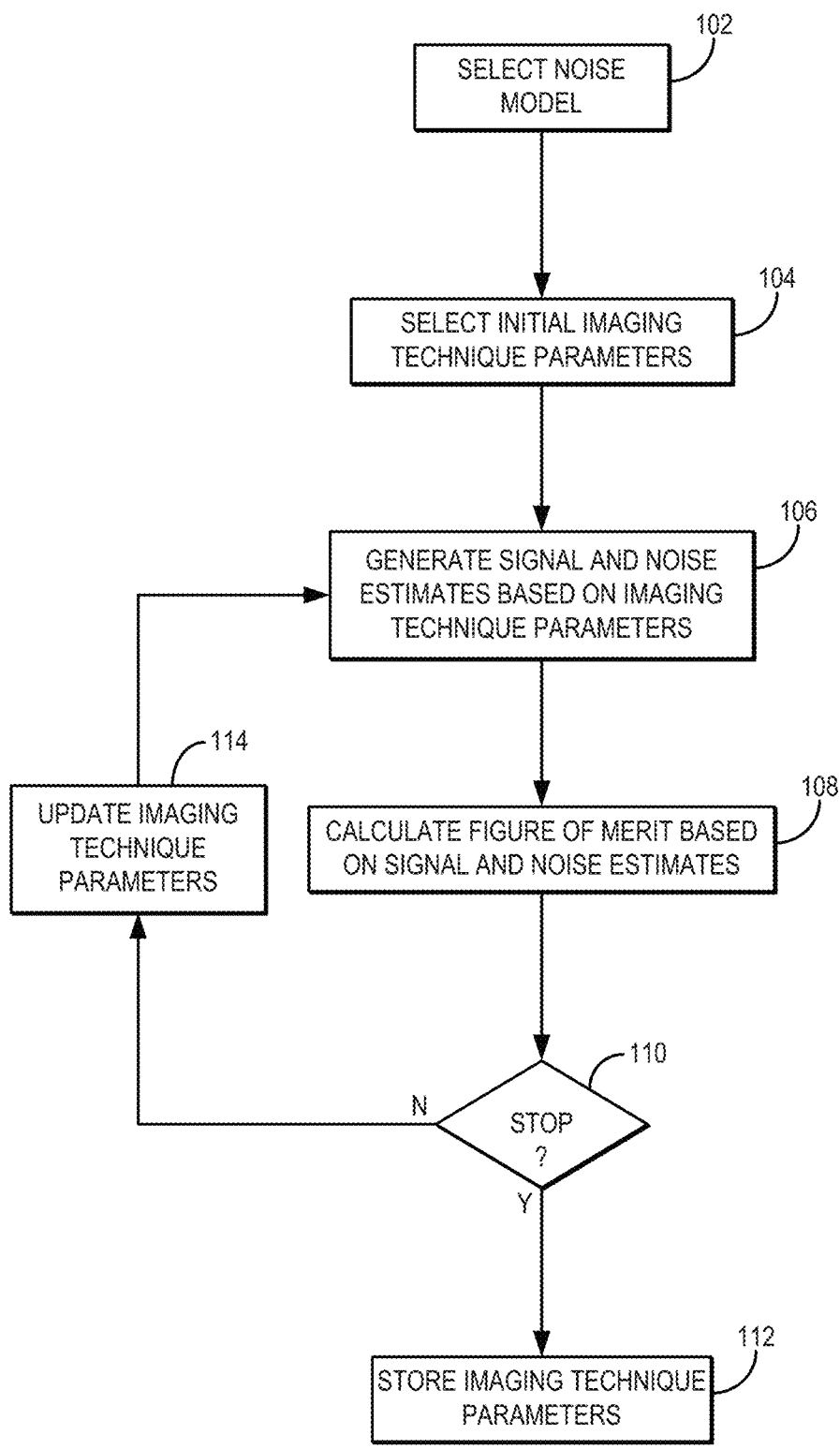
FIG. 1 is a flowchart setting forth the steps of an example method for optimizing photon-counting detector computed tomography ("PCCT") imaging technique parameters based on a noise propagation analysis.

Referring now to FIG. 1, a flowchart is illustrated as setting forth the steps of an example method for optimizing x-ray spectra settings, energy threshold settings, energy bin settings, or combinations thereof, using an optimization that is based at least in part on a signal estimation and noise propagation analysis. In general, the method includes using a signal estimation and noise propagation analysis to evaluate a number of different candidate configurations of imaging technique parameters. The signal estimation and noise propagation analysis is generally based on a noise model, such as one of the following example noise models. Thus, as indicated at step 102, the method includes selected a noise model to be implemented in the noise propagation analysis.

As one example, the noise model can be based on an acquisition scheme in which measurements are obtained on the same pixel and spectrum with N identical energy thresholds on the same detector element. In this scheme, the noise model is, $$\sigma^2 \propto \frac{1}{N(\text{bin})} = \frac{1}{N_L - N_H}; \qquad (1)$$

where $\sigma^2$ is the noise in PCCT images, $N_L$ is the photon count above the low-energy threshold, and $N_H$ is the photon count above the high-energy threshold.

As another example, the noise model can be based on an acquisition scheme in which cross-pixel or cross-spectrum measurements are obtained with M<N different energy thresholds on the same detector element. For this scheme, the noise model can be described as, $$\sigma^2 \propto \frac{(N_L + N_H)}{(N_L - N_H)^2}. \qquad (2)$$

In both of these example noise models, the desired signals (e.g., CT number, dual energy ratio) are estimated by known energy spectrum and detector response. Based on the selected noise model, the method proceeds to optimize the imaging technique parameters to maximize SNR, CNR, or both, or to minimize noise for different clinical tasks. An example of imaging technique parameters can include x-ray spectra parameters, energy threshold parameters, energy bin parameters, or combinations thereof.

The method thus includes selecting initial imaging technique parameters, as indicated at step 104. As mentioned above, the imaging technique parameters can include x-ray spectra parameters, energy threshold parameters, energy bin parameters, or combinations thereof. The imaging technique parameters can also include information based on the detector response of the photon-counting detectors used in a PCCT system and information about the object being imaged, including the size of the object and materials contained in the object.

In some embodiments, the imaging technique parameters also include the selection of the image reconstruction method to be used, post-processing methods to be used, or both. As one example, optimizing the imaging technique parameters can include selecting an iterative reconstruction technique, which may result in a more significant noise reduction than a filter backprojection reconstruction. By selecting such an iterative reconstruction technique, the other parameters (e.g., x-ray spectra settings, energy threshold settings, energy bin settings) can be more aggressively optimized because the iterative reconstruction will generally result in lower image noise.

As another example, optimizing the imaging technique parameters can also include selecting one or more post-processing methods, or the selection of such post-processing methods can influence the optimization of other parameters (e.g., x-ray spectra settings, energy threshold settings, energy bin settings). For instance, if the acquired data are to be processed to generate a monochromatic image, optimizing the imaging technique parameters can include optimizing the energy bin selection to select energy bins that are farther apart, thereby facilitating the generation of a monochromatic image.

Using the initial imaging technique parameters, signal and noise estimates are generated based on the initial imaging technique parameters, as indicated at step 106. As one example, the signal and noise estimates can be generated using a virtual PCCT scan. As another example, the signal and noise estimates can be generated using numerical simulations. A figure of merit value is then computed based on the signal and noise estimates. As an example, the figure of merit can include a signal-to-noise ratio ("SNR") or a contrast-to-noise ratio ("CNR"). The figure of merit value is then compared against a stopping criterion to determine whether the optimal imaging technique parameters have been achieved for the particular imaging task at hand, as determined at decision block 110. For instance, evaluating the stopping criterion can include comparing the figure of merit value in the current iteration with the figure of merit value computed from the previous iteration. If the optimal imaging technique parameters have been utilized for the particular imaging task at hand, as determined at decision block 110, then the imaging technique parameters are stored for use with the PCCT system, as indicated at step 112. Otherwise, the imaging technique parameters are updated at step 114 and new signal and noise estimates are generated using the updated imaging technique parameters.

As mentioned above, the final stored imaging technique parameters can be provided to a PCCT system to direct imaging of the object according to the stored imaging technique parameters.

As one example implementation of the foregoing method, the imaging technique parameters can be optimized to maximize the CNR achievable when using a particular contrast agent, such as iodine, gadolinium, or gold. In these examples, the CNR for a particular contrast agent can be maximized by optimizing the energy thresholds. Example optimizations are illustrated in FIGS. 2A-2C, which can be used to identify the optimal energy thresholds to maximize CNR for iodine (FIG. 2A), gadolinium (FIG. 2B), and gold (FIG. 2C) contrast agents.

Figures 3A, 3B, 3C:
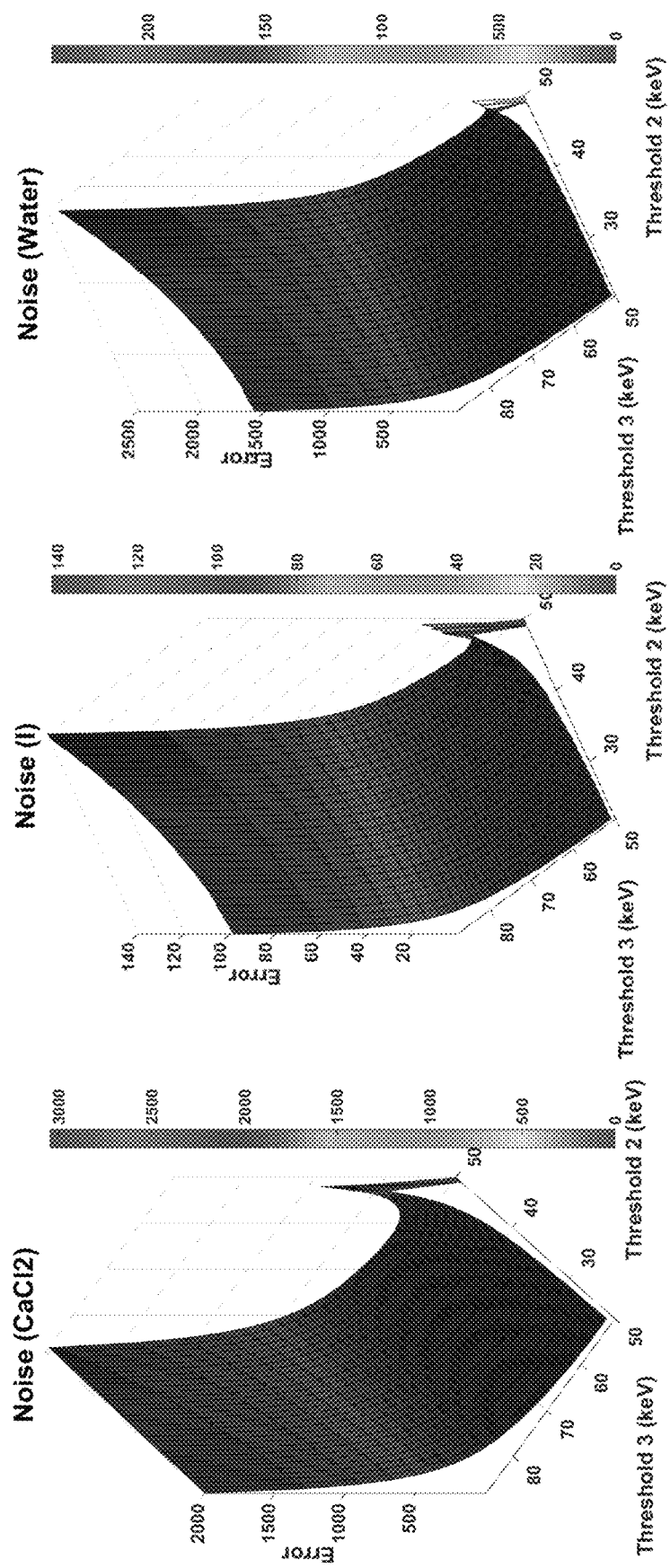
FIGS. 3A-3C illustrate examples of noise propagation analysis-based optimizations for two energy thresholds for different material decomposition tasks.

As another example, the imaging technique parameters can be optimized to minimize noise for material decomposition. In these examples, noise in basis material density maps can be minimized by optimizing two energy thresholds. Example optimizations are illustrated in FIGS. 3A-3C, which can be used to identify the optimal low-energy and high-energy thresholds to minimize noise for calcium chloride decompositions (FIG. 3A), iodine decompositions (FIG. 3B), and water decompositions (FIG. 3C).

Overall Cramer-Rao Lower Bound Analysis

As mentioned above, the optimization of imaging technique parameters for PCCT can also be based on an overall CRLB calculation. The CRLB calculation can be used to calculate the lowest bound of basis image noise for multi-energy x-ray transmission measurements at a single projection or ray. CT measurements, however, are different from x-ray transmission measurements. For instance, CT measurements involve a number of variations in different detector channels, projections, post-processing, and reconstruction methods. To date, CRLB has not been implemented to optimize PCCT imaging technique parameters while also taking into account these factors.

Figure 4:
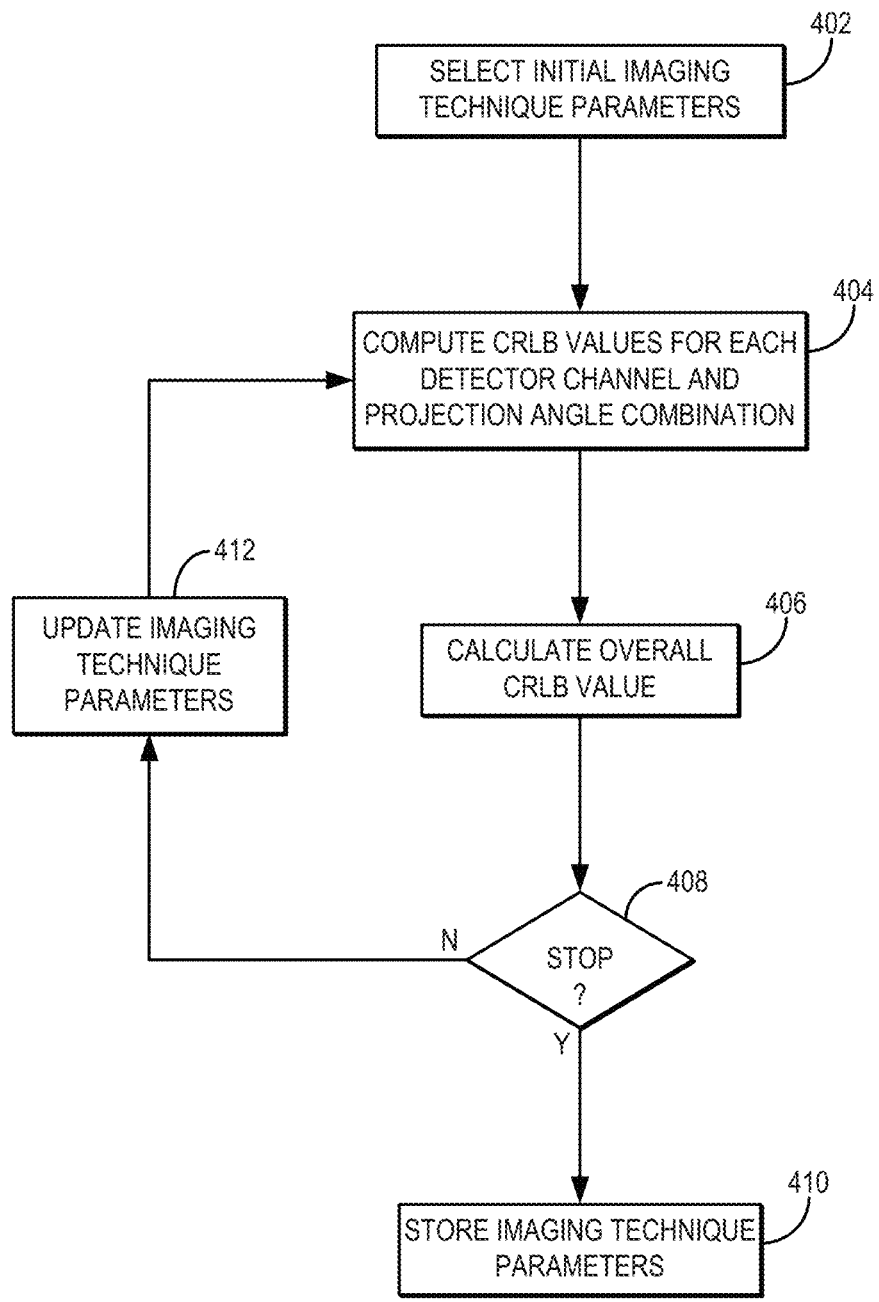
FIG. 4 is a flowchart setting forth the steps of an example method for optimizing PCCT imaging technique parameters based on an overall Cramer-Rao Lower Bound calculation.

Referring now to FIG. 4, a flowchart is illustrated as setting forth the steps of an example method for optimizing PCCT imaging technique parameters using an optimization based on an overall Cramer-Rao lower bound ("oCRLB") calculation. In this method, an overall CRLB measure, described below, is implemented to optimize the selection of imaging technique parameters for a PCCT system. In general, the oCRLB calculation algorithm can be used to optimize x-ray spectrum, energy thresholds, energy bins, or combinations thereof, for PCCT measurements. The optimization takes into consideration variations among detector channels, projections, reconstruction algorithms, or combinations thereof. The overall CRLB analysis can be implemented for different threshold configurations for calcium/iron/water material quantification.

Because of the large variations between detector channels, projection angles, and reconstruction kernels, one optimal energy threshold configuration for one single x-ray transmission measurement may not be the best one for another combination of detector channel and projection angle. The oCRLB calculation can be designed to account for those acquisition parameters and reconstruction methods.

The method begins with the selection of initial imaging technique parameters, as indicated at step 402. As mentioned above, the imaging technique parameters can include x-ray spectra parameters, energy threshold parameters, energy bin parameters, or combinations thereof. The imaging technique parameters can also include information based on the detector response of the photon-counting detectors used in a PCCT system, and information about the object being imaged, including the size of the object and materials contained in the object. As mentioned above, the imaging technique parameters can also include the selection of the image reconstruction method to be used, post-processing methods to be used, or both.

Using the initial imaging technique parameters, a CRLB calculation is performed for each combination of detector channel, projection angle, and different material attenuation, as indicated at step 404. Then, an oCRLB value is computed based on the CRLB calculations, as indicated at step 406. As an example, the oCRLB calculation is achieved as a weighted summation of the CRLB calculations, which consider the variations in attenuation, reconstruction kernel, and so on. As another example, the oCRLB calculation can be obtained as a reconstruction of a noise map based on the CRLB values at each view and each projection.

The oCRLB value is then compared against a stopping criterion to determine whether the optimal imaging technique parameters have been achieved for the particular imaging task at hand, as determined at decision block 408. If the optimal imaging technique parameters have been reached, then the imaging technique parameters are stored for use with the PCCT system, as indicated at step 410. Otherwise, the imaging technique parameters are updated at step 412 and a new CRLB computation is performed based on the updated imaging technique parameters and its results analyzed using the oCRLB method. It is contemplated that the imaging technique parameters with the lowest oCRLB will yield the best results; thus, the optimization can be based on identifying the imaging technique parameters that result in the minimum oCRLB value.

As mentioned above, the final stored imaging technique parameters can be provided to a PCCT system to direct imaging of the object according to the stored imaging technique parameters.

As one example, the oCRLB-based optimization can be used to optimize the PCCT scan parameter selection for a material decomposition task, such as for a calcium/iron/water material decomposition, which is relevant to many clinically important tasks, such as vascular plaque quantification and liver iron overload measurement. The oCRLB calculation can be used to predict four energy configurations with different rank on material decomposition accuracy.

PCCT experiments have shown that the oCRLB approach can be used to optimize energy threshold configurations for material decomposition, which is relevant for many different clinical tasks, including CT perfusion imaging, virtual non-contrast imaging, renal stone characterization, and so on.

Virtual Scan and Model Observer Analysis

As mentioned above, the optimization of imaging technique parameters for PCCT can also be based on model observers. The model observer calculates a figure of merit that is related to a specific imaging task based on the signal and noise properties of the images to which the model observer is applied. The imaging technique parameters defining an imaging technique in a PCCT system, which affect both signal and noise properties of the images to be acquired, can then be optimized by maximizing the figure of merit in the model observer.

Figure 5:
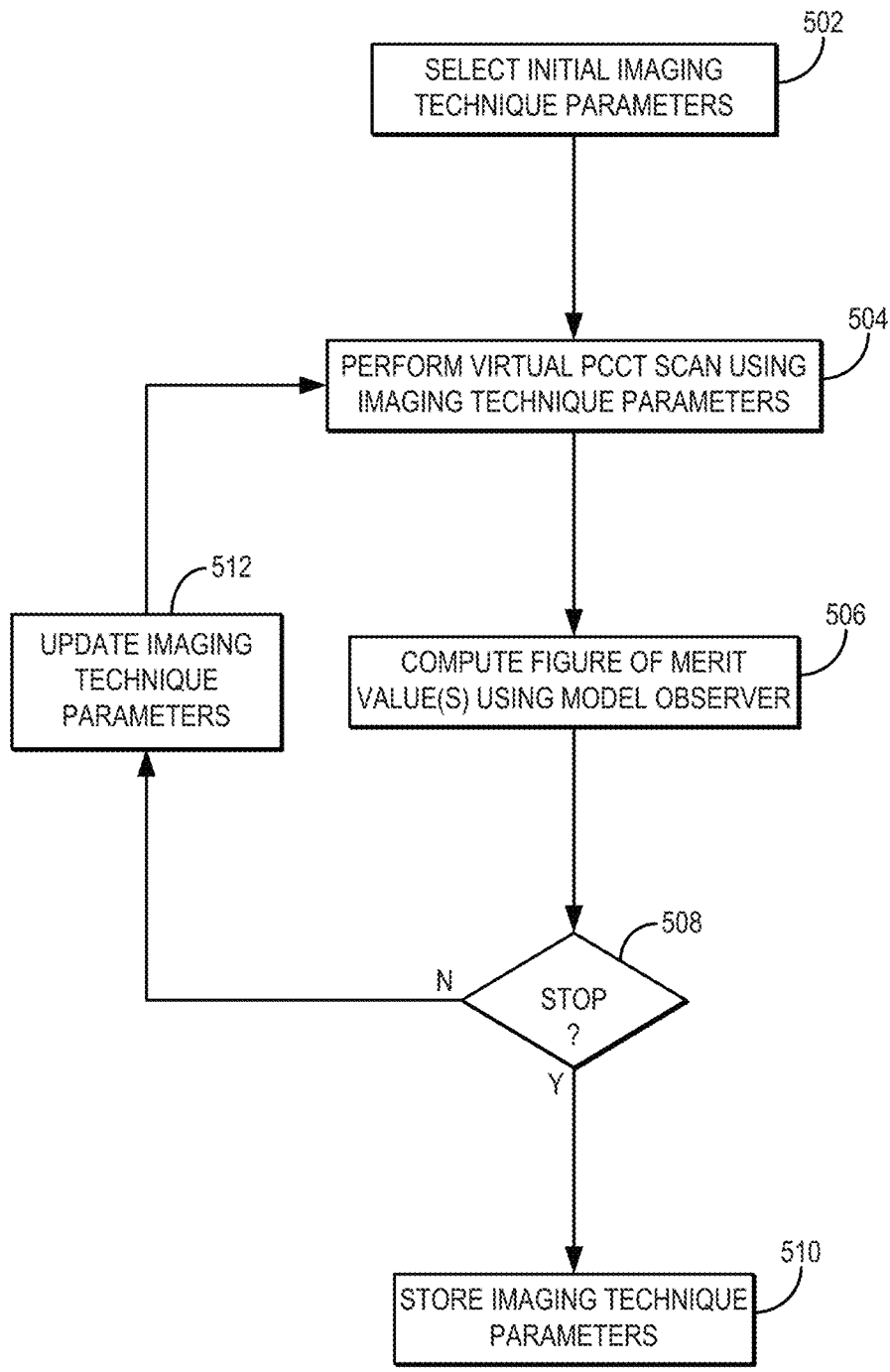
FIG. 5 is a flowchart setting forth the steps of an example method for optimizing PCCT imaging technique parameters based on one or more model observers.

Referring now to FIG. 5, a flowchart is illustrated as setting forth the steps of an example method for optimizing PCCT imaging technique parameters using an optimization based on a model observer. In this method, a model observer is implemented to optimize the selection of imaging technique parameters defining an imaging technique for a PCCT system. In general, the model observer calculation algorithm can be used to optimize x-ray spectrum, energy thresholds, energy bins, or combinations thereof, for PCCT measurements. The optimization takes into consideration variations among detector channels, projections, reconstruction algorithms, or combinations thereof. As mentioned above, the imaging technique parameters can also include the selection of the image reconstruction method to be used, post-processing methods to be used, or both.

The method begins with the selection of initial imaging technique parameters, as indicated at step 502. As mentioned above, the imaging technique parameters can include x-ray spectra parameters, energy threshold parameters, energy bin parameters, or combinations thereof, which may define an imaging technique. The imaging technique parameters can also include information based on the detector response of the photon-counting detectors used in the PCCT system, and information about the object being imaged, including the size of the object and materials contained in the object.

Using the imaging technique parameters, a virtual PCCT scan is performed to generate estimates of signal and noise based on the imaging technique parameters, as indicated at step 504. Multiple noise realizations are computed for these imaging technique parameters. A model observer is then applied to the images obtained using the virtual scans, and a figure of merit is calculated for a specific imaging task, as indicated at step 506. Examples of figures of merit include, but are not limited to, area under the receiving operating characteristic curve, detectability index, or percent correct.

The figure of merit value of the model observer is then compared against a stopping criterion to determine whether the optimal imaging technique parameters have been achieved for the particular imaging task at hand, as determined at decision block 508. If the optimal imaging technique parameters have been reached, then the imaging technique parameters are stored for use with the PCCT system, as indicated at step 510. Otherwise, the imaging technique parameters are updated at step 512 and a new virtual scan is performed and its results analyzed using the model observer method. It is contemplated that the imaging technique parameters yielding the highest figure of merit value will yield the best results; thus, the optimization can be based on identifying the imaging technique parameters that result in the maximal figure of merit value.

As mentioned above, the final stored imaging technique parameters can be provided to a PCCT system to direct imaging of the object according to the stored imaging technique parameters.

As one example, the model-observer-based optimization can be used to optimize the PCCT imaging technique parameter selection for a material decomposition task, such as for a calcium/iron/water material decomposition, which is relevant to many clinically important tasks, such as vascular plaque quantification and liver iron overload measurement. As another example, the model-observer-based optimization can be used to optimize the PCCT imaging technique parameter selection for a detection task with contrasts made of nanoparticles, such as gold, bismuth, and tungsten nanoparticles.

The optimization tools described here can be used to optimize energy threshold or energy bin settings for a chosen x-ray tube spectrum based on patient or phantom size, the material of interest, and the location of the targeted material.

Figure 6A:
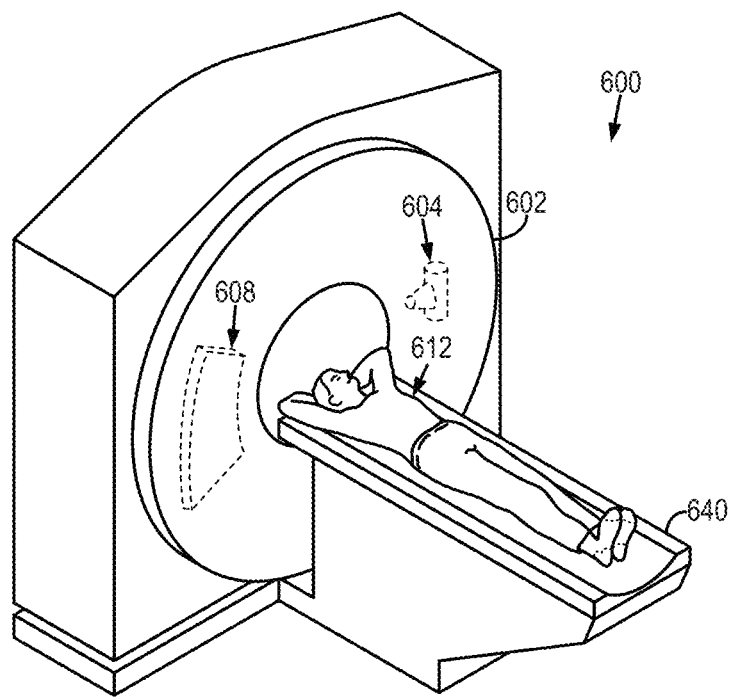
FIGS. 6A and 6B illustrate an example CT system that can be configured to operate as a PCCT system.
Figure 6B:
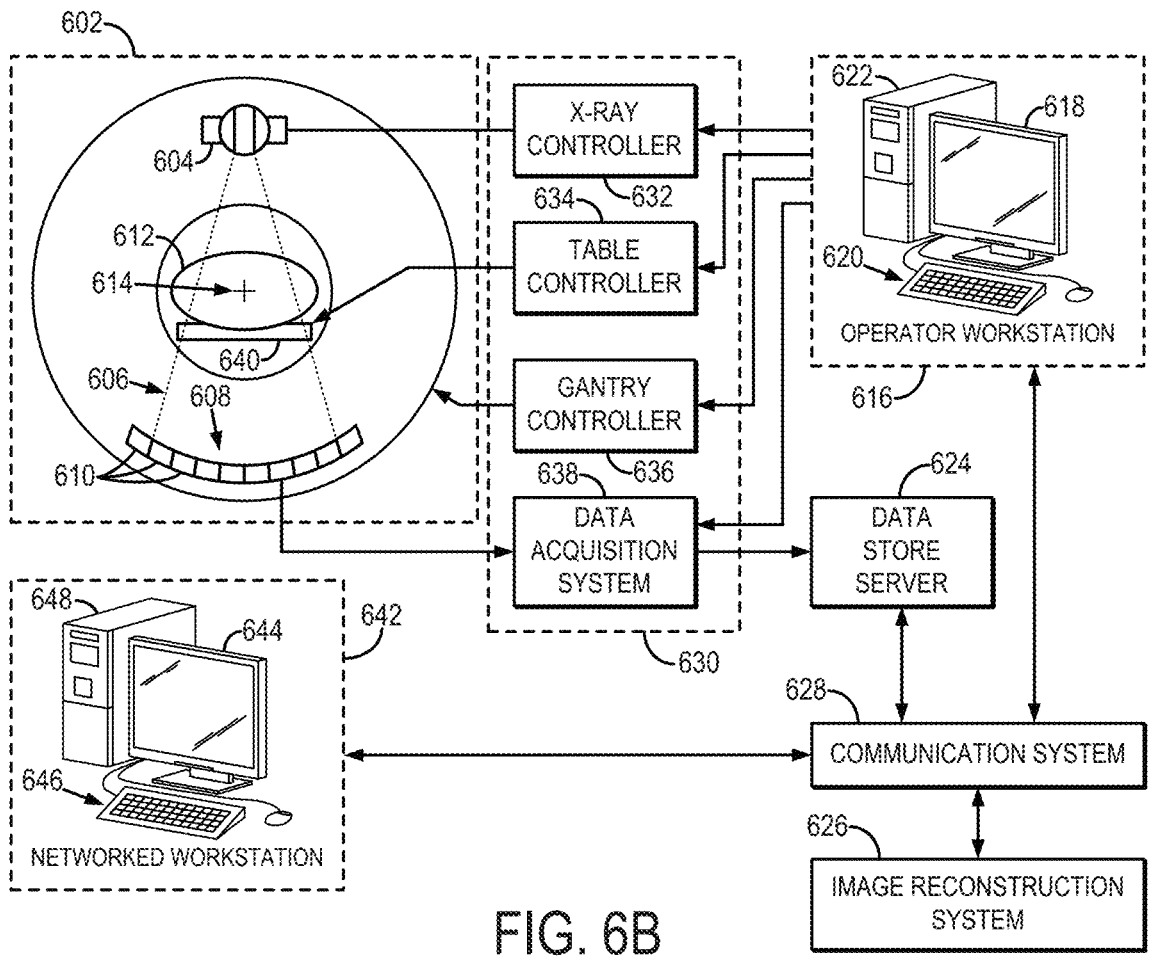

Referring particularly now to FIGS. 6A and 6B, an example of an x-ray computed tomography ("CT") imaging system 600 is illustrated. The CT system includes a gantry 602, to which at least one x-ray source 604 is coupled. The x-ray source 604 projects an x-ray beam 606, which may be a fan-beam or cone-beam of x-rays, towards a detector array 608 on the opposite side of the gantry 602. The detector array 608 includes a number of x-ray detector elements 610. Together, the x-ray detector elements 610 sense the projected x-rays 606 that pass through a subject 612, such as a medical patient or an object undergoing examination, that is positioned in the CT system 600. Each x-ray detector element 610 produces an electrical signal that may represent the intensity of an impinging x-ray beam and, hence, the attenuation of the beam as it passes through the subject 612. In some configurations, each x-ray detector 610 is capable of counting the number of x-ray photons that impinge upon the detector 610. During a scan to acquire x-ray projection data, the gantry 602 and the components mounted thereon rotate about a center of rotation 614 located within the CT system 600.

The CT system 600 also includes an operator workstation 616, which typically includes a display 618; one or more input devices 620, such as a keyboard and mouse; and a computer processor 622. The computer processor 622 may include a commercially available programmable machine running a commercially available operating system. The operator workstation 616 provides the operator interface that enables scanning control parameters to be entered into the CT system 600. In general, the operator workstation 616 is in communication with a data store server 624 and an image reconstruction system 626. By way of example, the operator workstation 616, data store sever 624, and image reconstruction system 626 may be connected via a communication system 628, which may include any suitable network connection, whether wired, wireless, or a combination of both. As an example, the communication system 628 may include both proprietary or dedicated networks, as well as open networks, such as the internet.

The operator workstation 616 is also in communication with a control system 630 that controls operation of the CT system 600. The control system 630 generally includes an x-ray controller 632, a table controller 634, a gantry controller 636, and a data acquisition system 638. The x-ray controller 632 provides power and timing signals to the x-ray source 604 and the gantry controller 636 controls the rotational speed and position of the gantry 602. The table controller 634 controls a table 640 to position the subject 612 in the gantry 602 of the CT system 600.

The DAS 638 samples data from the detector elements 610 and converts the data to digital signals for subsequent processing. For instance, digitized x-ray data is communicated from the DAS 638 to the data store server 624. The image reconstruction system 626 then retrieves the x-ray data from the data store server 624 and reconstructs an image therefrom. The image reconstruction system 626 may include a commercially available computer processor, or may be a highly parallel computer architecture, such as a system that includes multiple-core processors and massively parallel, high-density computing devices. Optionally, image reconstruction can also be performed on the processor 622 in the operator workstation 616. Reconstructed images can then be communicated back to the data store server 624 for storage or to the operator workstation 616 to be displayed to the operator or clinician.

The CT system 600 may also include one or more networked workstations 642. By way of example, a networked workstation 642 may include a display 644; one or more input devices 646, such as a keyboard and mouse; and a processor 648. The networked workstation 642 may be located within the same facility as the operator workstation 616, or in a different facility, such as a different healthcare institution or clinic.

The networked workstation 642, whether within the same facility or in a different facility as the operator workstation 616, may gain remote access to the data store server 624 and/or the image reconstruction system 626 via the communication system 628. Accordingly, multiple networked workstations 642 may have access to the data store server 624 and/or image reconstruction system 626. In this manner, x-ray data, reconstructed images, or other data may be exchanged between the data store server 624, the image reconstruction system 626, and the networked workstations 642, such that the data or images may be remotely processed by a networked workstation 642. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for determining imaging technique parameters for a photon-counting computed tomography (PCCT) system, the steps of the method comprising:
   (a) selecting imaging technique parameters for the PCCT system;
   (b) computing optimal imaging technique parameters using an optimization in which each iteration of the optimization includes:
      (i) computing a Cramer-Rao Lower Bound (CRLB) value for each of a plurality of different combinations of detector channels and projection angles associated with the PCCT system and based on the imaging technique parameters;
      (ii) computing an overall CRLB value as a weighted summation of the CRLB values;
      (iii) evaluating a stopping criterion based on the overall CRLB value;
      (iv) updating the imaging technique parameters when the stopping criterion is not satisfied; and
      (v) storing the imaging technique parameters as the optimal imaging technique parameters for later use with the PCCT system when the stopping criterion is satisfied.

2. The method as recited in claim 1, wherein the imaging technique parameters include at least one of x-ray spectra parameters, energy threshold parameters, or energy bin parameters.

3. The method as recited in claim 1, wherein the stopping criterion is satisfied when the overall CRLB value is minimized.

4. The method as recited in claim 1, wherein the imaging technique parameters are associated with detector response of photon-counting detectors of the PCCT system.

5. The method as recited in claim 1, wherein the imaging technique parameters are associated with properties of an object to be imaged with the PCCT system.

6. The method as recited in claim 5, wherein the properties of the object comprise at least one of a size of the object or a materials contained in the object.

7. The method as recited in claim 1, wherein step (b) is repeated in order to determine a plurality of sets of optimal imaging technique parameters each having a different rank on material decomposition accuracy.

8. The method as recited in claim 7, wherein each of the plurality of sets of optimal imaging technique parameters is associated with each of a plurality of different materials in a material decomposition task.

9. The method as recited in claim 8, wherein the plurality of different materials comprises at least two of calcium, iron, and water.

* * * * *